United States Patent [19]

Vezina

[11] 3,960,005

[45] June 1, 1976

[54] ULTRASONIC TESTING DEVICE FOR INSPECTING THERMIT RAIL WELDS

[75] Inventor: Georges E. Vezina, Laval-des-Rapides, Canada

[73] Assignee: Canac Consultants Limited, Montreal, Canada

[22] Filed: Aug. 9, 1974

[21] Appl. No.: 496,310

[52] U.S. Cl. .............................................. 73/67.7
[51] Int. Cl.² ........................................ G01N 29/04
[58] Field of Search............ 73/67.7, 67.8 R, 67.8 S, 73/67.9, 67.5 R, 71.5 US

[56] References Cited
UNITED STATES PATENTS

| | | | |
|---|---|---|---|
| 3,028,751 | 4/1962 | Joy.................................. | 73/67.7 X |
| 3,135,109 | 6/1964 | Werner............................ | 23/67.8 S |
| 3,251,220 | 5/1966 | Joy.................................. | 73/67.7 |
| 3,279,242 | 10/1966 | Megoloff......................... | 73/67.8 S |
| 3,415,110 | 12/1968 | Cowan............................. | 73/67.8 S |
| 3,552,191 | 1/1971 | Heseding ........................ | 73/67.7 |
| 3,608,361 | 9/1971 | Krautkramer et al. .............. | 73/67.7 |
| 3,739,628 | 6/1973 | Saglio ............................. | 73/67.7 |

*Primary Examiner*—Richard C. Queisser
*Assistant Examiner*—Stephen A. Kreitman
*Attorney, Agent, or Firm*—Larson, Taylor & Hinds

[57] ABSTRACT

An ultrasonic testing device for inspecting thermit rail welds in a track is disclosed. The device may be passed over the top of a rail weld in a track to indicate whether there are any faults in the weld. The device includes a longitudinal shoe which may be placed lengthwise along the top surface of the rail, a transmitter which transmits an ultrasonic energy pulse and a receiver for receiving the ultrasonic energy pulse, the transmitter and receiver being positioned and aimed so that an energy pulse is directed downwards towards a location on the under surface of the rail and reflects upwards as an echo pulse so that it is received by the receiver. The indication of the transmittal and receival of the pulse is shown on a cathode ray tube or multichannel pen recorder. A method of inspecting the thermit rail weld is also disclosed. This includes the transmission of a pulse at an angle of at least 45° through the weld and receiving an echo of this pulse which has been reflected off the bottom surface of the rail.

12 Claims, 11 Drawing Figures

ULTRASONIC TESTING DEVICE FOR INSPECTING THERMIT RAIL WELDS

This invention relates to ultrasonic weld testing and in particular to an ultrasonic testing device which may be passed over the top of a rail weld in a track and which indicates if there are any faults in the weld.

The inspection of railroad tracks by ultrasonic testing is well known. Previous testing, however, has been primarily used to detect imperfections in the rail itself and the equipment generally includes a transmitter mounted above the rail directed vertically downwards and a receiver adjacent or the same unit as the transmitter. Such a device detects such defects as bolt hole breaks, head end web separations and horizontal split heads. Other types of testing devices have transmitters mounted at an angle above the rail and detect defects in the rail surface or defects located directly under the surface, including burns, shelling or other surface discontinuities. Whereas these devices serve the purpose for which they are intended, they are not suitable for inspecting welds between two rails. Rails are generally welded into reasonably long lengths by flash butt welding in an assembly area. The failure rate of flush butt welds which are welded under controlled conditions is very low. However, thermit welds are usually used in the field to join track together, and here failure rate is higher in view of the difficulty in strictly controlling all the parameters, including temperature of the rail at the time of the weld. Ultrasonic examination of thermit rail welds in a track presents problems, first because the welded structure causes considerable attenuation and scattering of the ultrasonic energy pulses, and second because the physical aspects and shape of the weld is such that it causes numerous non-revelent reflections which with all existing ultrasonic rail testing equipment tend to show that every thermit rail weld is a defective weld.

It is, therefore, an object of the present invention to provide a device for inspecting thermit welds in rail track which overcomes the aforementioned problem. It is a further object to provide a device for determining lack of fusion and porosity in a rail and distinguishing one from the other. Yet a further object is to provide a device for inspecting welds in rail track by moving an ultrasonic testing device along the top of the rail over the weld so that lack of fusion or porosity in the weld appears on a cathode ray tube display or a multichannel chart recorder.

According to the present invention, these objects and others can be accomplished by providing an ultrasonic testing device for inspecting thermit rail welds in a track, comprising a longitudinal shoe adapted to be placed lengthwise along the top surface of a rail, a means for transmitting an ultrasonic energy pulse and a means for receiving an ultrasonic energy pulse spaced a predetermined distance apart along the longitudinal shoe, the means for transmitting an ultrasonic energy pulse adapted to direct the pulse in a downwards path towards a location on the under surface of the rail below the midpoint between the means for transmitting a pulse and the means for receiving a pulse, the means for receiving a pulse adapted to receive an echo of the pulse reflecting from the location on the under surface of the rail, and means for indicating the transmission of the pulse, the receiving of the echo of the pulse, and the time interval for the pulse to pass downward through the rail and the echo of the pulse to pass upward through the rail.

The present invention also provides a method of inspecting a thermit rail weld in a track comprising transmitting an ultrasonic energy pulse from the top of the track at one side of the thermit rail weld at an angle of at least 45° through the weld, receiving on the top of the track at the other side of the thermit rail weld an echo pulse of the ultrasonic energy pulse reflecting from the underside of the rail indicating transparency in the weld.

The advantage of this invention, both as to its construction and mode of operation, will be readily appreciated as the same becomes better understood by reference to the following detailed description when considered in connection with the accompanying drawings which illustrate embodiments of the invention.

Figure 1:
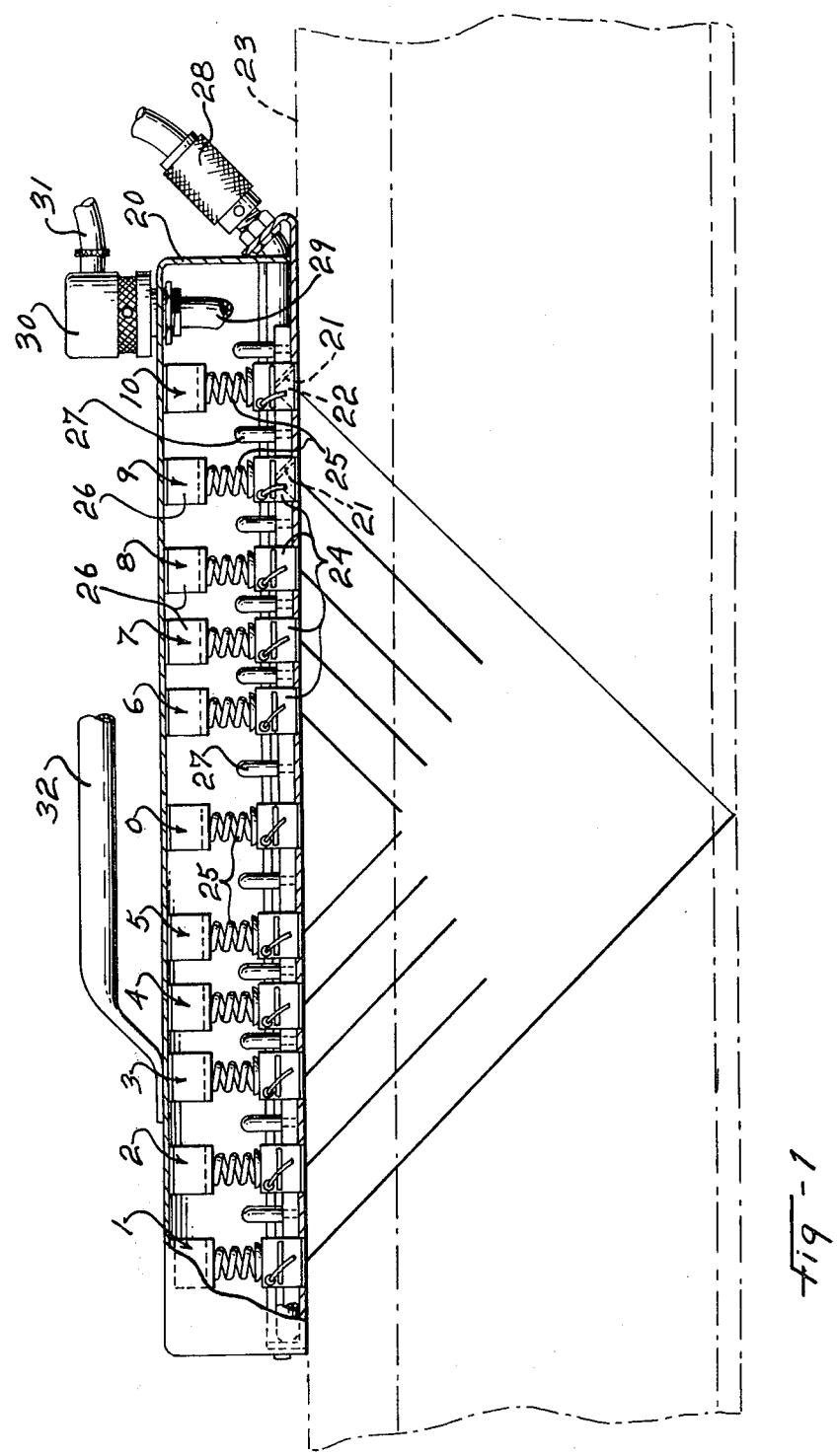
FIG. 1 is a side elevation, partly in section, showing one embodiment of an ultrasonic testing device of the present invention.

Referring now to FIG. 1, an ultrasonic testing device for inspecting thermit welded joints in rails is shown comprisisng a longitudinal shoe or sheet metal housing 20, containing a total of eleven transducer probes. Each probe can act as either a transmitter, a receiver, or a combination transmitter/receiver for ultrasonic energy pulses. In the centre of the housing 20 is located central probe 0 having a transducer mounted behind a flat prism such that an ultrasonic energy pulse is transmitted or received vertically downwards. The prism is preferably made of a plastic material, but is always capable of transmitting ultrasonic energy pulses. At the extreme ends of the housing 20 are mounted outside probe 1 and outside probe 10, both equidistant apart from central probe 0. Referring to the cross-section of outside probe 10, a transducer 21 is mounted on an angular prism 22 so that the pulse from the transducer 21 is transmitted into the rail 23 directly beneath the housing 20 at a downward angle towards the under surface of the rail in a direction towards the centre of the housing 20 directly beneath the central probe 0. In FIG. 1 the angle of the pulse path from outside probe 10 is shown to be approximately 45° or greater, the important point being that the pulse path from the transmitting transducer hits the under surface of the rail 23 directly beneath the central probe 0. When the pulse from the transmitting transducer 21 hits the under surface of the rail 23 it rebounds at the same angle of incidence that it hits the under surface of the rail and thus the probe path directs the pulse to the receiving transducer in outside probe 1 which is equidistant from the central probe 0. Similarly, if the signal is transmitted from the transducer in outside probe 1 it is received by the transducer 21 in outside probe 10.

The transducer 21 and angular prism 22 shown in outside probe 10 are mounted in a sealed container 24 having a spring 25 pressing down on the container 24 from a spring holding locator 26 which in turn is supported at the top of the housing 20. Thus, when the device rests on the rail 23 the sealed container 24 containing the transducer 21 and angular prism 22 are always pressed firmly down on the top surface of the rail for maximum contact between the angular prism 22 and the rail 23. To insure better performance of the ultrasonic probe signal passing from the transducer to the rail, a liquid, preferably water, is passed from wetting outlets 27 located in front and behind each probe. The liquid provides a thin liquid film between the angle blocks and the rail surface. A pipe connector 28 provides a supply of liquid to each of the outlets 27. The transducers in each probe are connected by cables 29 inside the housing 20 to a conduit connector 30 and hence by means of a multiple flexible cable 31 to the main circuitry of the device. A support bracket 32 is attached to the top of the housing 20, either to support the device as a hand-held probe device or, alternatively, for mounting on the underside of a special rail test car.

As seen from FIG. 1, the arrangement of the transducer probes in such that outer probes 1 or 10 transmit or receive pulses in a path which meets at the under surface of the rail directly beneath probe 0. Additional probes 2 to 9, referred to as porosity seeking probes, transmit or receive pulses along paths which meet beneath central probe 0 just above the base of the rail. The height of the rail is divided into four portions; probes 2 and 9 cover the lowest portion, probes 3 and 8 the next portion, probes 4 and 7 the next portion and probes 5 and 6 the top portion.

In operation of the device, the housing 20 containing the eleven probes is placed on a rail 23 and moved across a thermit welded joint. An ultrasonic energy pulse is transmitted from the transducer in outside probe 1. The pulse travels in a path down to the under surface of the rail 23. It then rebounds off the under surface of the rail in a path that takes it up to be received by the transducer 21 in outside probe 10. Thus, a cathode ray tube display shows two blips, the first blip being the pulse transmitted from the transducer in outside probe 1, the second blip being the pulse received by the transducer 21 in probe 10. As the device moves along the rail the pulse path from outside probe 1 passes through the top of the thermit weld down to the under surface of the rail 23, bounces off the under surface of the rail 23 producing an echo pulse which is received by the transducer in outside probe 10. The device continues moving along the rail until the thermit weld is exactly in the centre between outside probes 1 and 10 and then as the device proceeds further along the rail, the pulse from outside probe 1 hits the under surface of the rail before the thermit weld. If there is lack of fusion between the weld and the rail or if there are areas of porosity in the weld then the pulse either passing from outside probe 1 to the under surface of the rail or, alternatively, passing from the under surface of the rail up to outside probe 10 is stopped. The transparency of the weld is broken, and the cathode ray tube display shows only one pulse, that being the transmission pulse from the transducer in outside probe 1 rather than the pulse received at outside probe 10. "Transparency in the weld" in this context is the ability of ultrasonic energy pulses to pass through the weld.

The exact location of a weld defect is determined by the cathode ray tube display by relating the position of the probe assembly relative to the weld location and the particular probe transducer indicating the presence of a defect.

Another ultrasonic energy pulse is transmitted from central probe 0 directly downwards, and under normal circumstances the transducer in the central probe 10 also acts as a receiver and receives the echo pulse rebounding off the under surface of the rail. Thus, a cathode ray tube display shows the pulse transmitted from central probe 0; then, after the time it takes the pulse to move through the rail to the under surface and rebound back again to the central probe 0, an echo pulse occurs on the display. When the central probe 0 is directly over a thermit weld no echo pulse is received from rebounding off the under surface of the rail because the structure of the thermit weld is such that it does not easily allow the transmission of ultrasonic energy pulses, although pulses may pass at an angle through the weld structure such as pulses from outside probe 1, outside probe 10 or the porosity seeking probes 2 to 9. Pulses from the porosity seeking probes 2 to 9 follow signal paths at angles of 45° or greater and pass through good welds continuing on to the under surface of the rail where they rebound but the echo pulses do not directly strike any of the other probes in the unit. Probe 2 is matched with probe 9, probe 3 with probe 8, probe 4 with probe 7, and probe 5 with probe 6. At that point where the central probe 0 is directly over a thermit weld in the rail, pulses are transmitted from porosity seeking probes 2, 3, 4 and 5. If there are no areas of porosity in the weld, there is no echo pulse detected by porosity seeking probes 6, 7, 8 and 9. This does not mean that the weld is good, because if there is lack of fusion in the weld then again there would still be no echo pulse detected by probes 6, 7, 8 and 9, as the pulses from probes 2, 3, 4 and 5 rebound off the point where there is lack of fusion back towards the under surface of the rail and rebound back again in the direction from which they came but on a different plane. If, however, there are areas of porosity in the weld, these areas generally comprise small round or oval-shaped bubbles of air trapped in the weld. When a signal pulse hits such an area, then as a known phenomenon the pulse is spread out sending echo pulses in all directions. One of these echo pulses from the point of porosity is picked up by the matching receiver transducer in the porosity seeking probe 6, 7, 8 or 9, and thus appears on a cathode ray tube display. As the porosity seeking probes 2 to 5 cover the different portions of the height of rail, then it can be determined in which portion the porosity occurs. The cathode ray tube display indicates a first blip for the transmission of the pulse and a second blip if there is an area of porosity; the distance of the second blip from the first blip indicates to an operator which of the porosity seeker probes has received the echo signal and thus which portion of the rail has the porosity. Thus, outside probes 1 and 10 indicate lack of fusion or porosity in a weld by the disappearance of an echo pulse from the under surface of the rail; porosity seeking probes 2 to 9 determine porosity only in a weld by the appearance of an echo pulse reflected off the area of porosity; and probe 0 is a location probe to indicate when the device is directly over the thermit weld. If no echo pulse appears from the outside probes, and no echo pulses occur from any of the porosity seeking probes, then there is likely to be lack of fusion between the weld and the rail or a crack in the weld.

Figure 3:
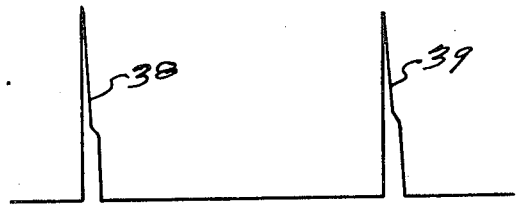
FIG. 3 illustrates the display on a cathode ray tube of the testing device shown in FIG. 2.
Figure 2:
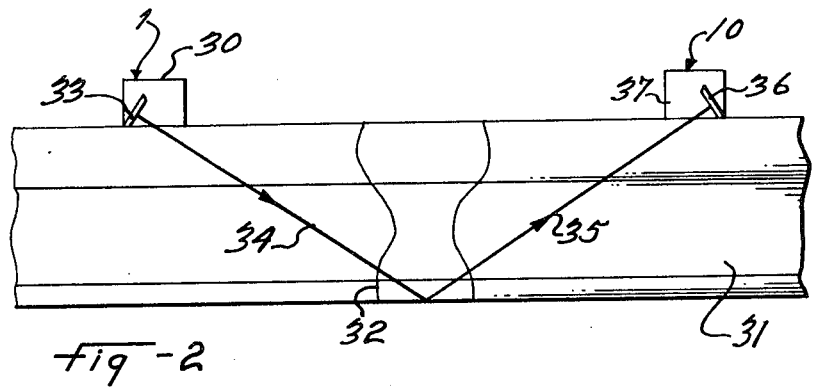
FIG. 2 is a schematic illustration showing the ultrasonic energy path below a testing device centred over a thermit rail weld.
Figure 5:
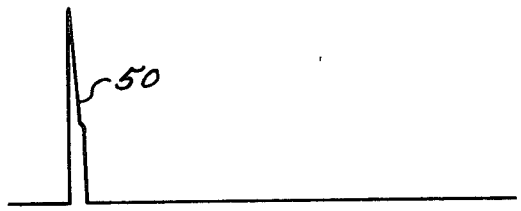
FIG. 5 illustrates the display on a cathode ray tube of the testing device shown in FIG. 4.
Figure 4:
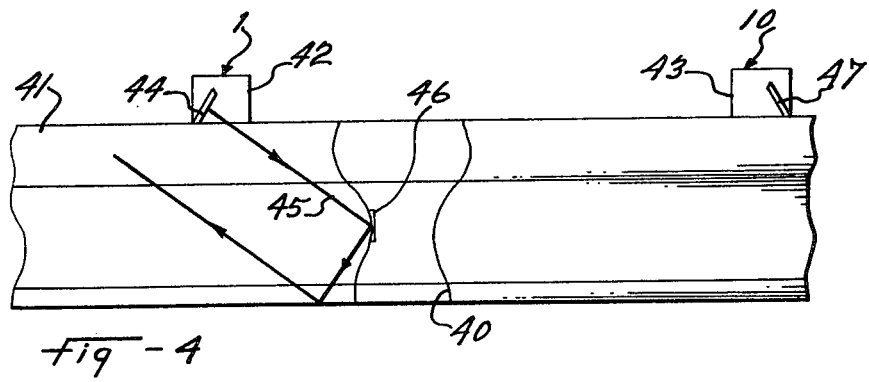
FIG. 4 is a schematic illustration showing the ultrasonic energy path below a testing device moved to the right of a thermit rail weld.

Referring now to FIGS. 2 and 3, a testing device with an outside probe 1, 30 shown in FIG. 2, is positioned above a rail 31 having a thermit weld 32 directly in the centre of the device. A pulse from the transmitting transducer 33 in probe 1, 30, follows a signal path 34 to the under surface of the rail 31 at a point in the centre of the thermit weld 32; an echo pulse rebounds off the bottom of the rail 31 and follows a path 35 striking the receiving transducer 36 in the outside probe 10 37. A display of such a pulse is shown in FIG. 3. This display appears on a cathode ray tube and shows a first blip 38 produced by the pulse being transmitted from the transducer 33 in probe 1 30 and a second blip 39 produced by the echo pulse striking the transducer 36 in probe 10, 37. The space between the two blips is a representation of the distance travelled by the pulse and echo pulse through the rail along the signal paths 34 and 35. Another situation is shown in FIGS. 4 and 5, where a thermit weld 40 is located off the centre of the device between the outside probe 1 42 and the outside probe 10 43. A pulse from the transducer 44 in the probe 1 42 follows a signal path 45 until it strikes a point 46 where there is lack of fusion between the rail 41 and the weld 40. The pulse cannot pass through this area where there is no fusion and thus rebounds downwards to strike the underside of the rail 41 and then rebounds again and follows a path at an angle practically parallel to signal path 43 from the transducer 44. Thus, no echo pulse is received by the transducer 47 in probe 10, 43. A display of such a pulse is shown in FIG. 5 where a first blip 50 represents the pulse transmitted from the transducer 44 in probe 1, 42 but no second blip occurs, and this indicates there is a fault in the weld area which is deflecting the pulse. This fault could be a crack in the weld or a point where lack of fusion occurs. Alternatively, this could also be an area of porosity in the weld which deflects the pulse passing through the weld. When the central probe 0 is directly over the thermit weld, the pulses from porosity seeking probes 2, 3, 4 and 5 show whether or not there is porosity in the weld rather than a weld crack or lack of fusion. If there is a weld crack or lack of fusion in the weld then no echo pulses are received by porosity seeking probes 6, 7, 8 and 9. Thus, the device distinguishes between porosity and lack of fusion or cracks in a thermit weld.

Figure 7:
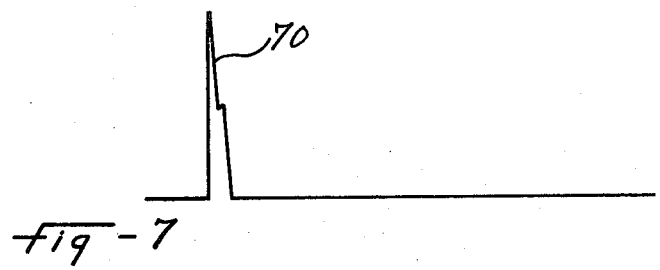
FIG. 7 illustrates the display on a cathode ray tube of the testing device shown in FIG. 6.
Figure 6:
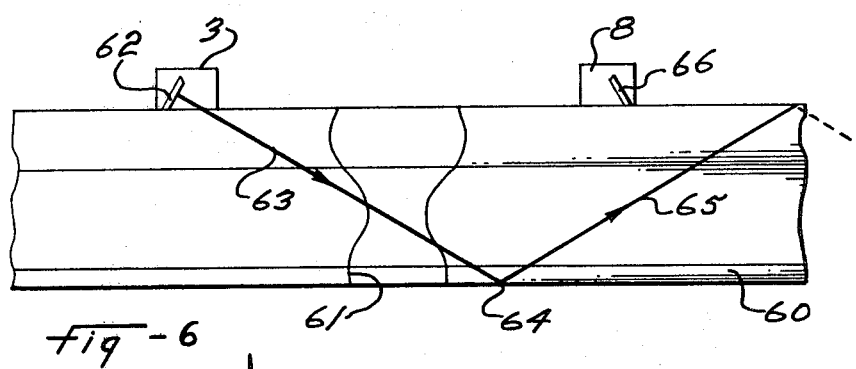
FIG. 6 is a schematic illustration showing the ultrasonic energy path from a porosity seeking transducer in a testing device finding no porosity in a thermit rail weld.
Figure 9:
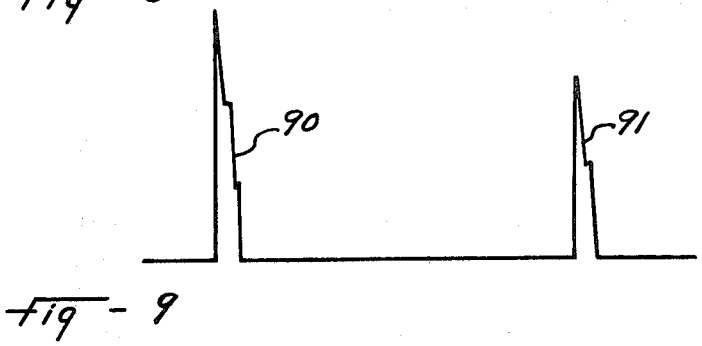
FIG. 9 illustrates the display on a cathode ray tube of the testing device shown in FIG. 8.
Figure 8:
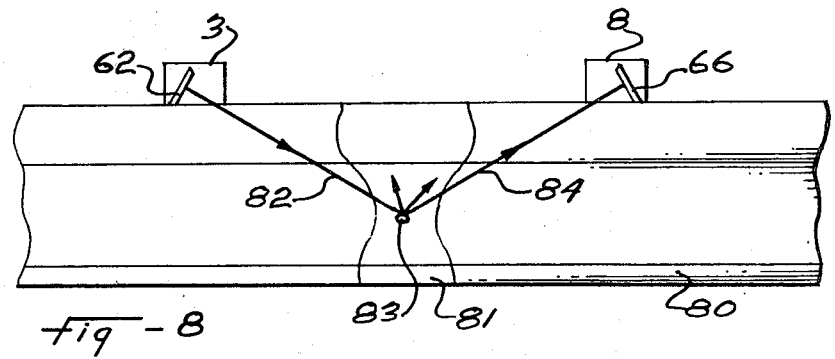
FIG. 8 is a schematic illustration showing the ultrasonic energy path from a porosity seeking transducer in a testing device finding an area of porosity in a thermit rail weld.

A testing device is shown in FIG. 6 with porosity seeking probes 3 and 8 positioned above a rail 60 having a thermit weld 61 in the centre of the device. A pulse from the transmitting transducer 62 in probe 3 follows a signal path 63 through the thermit weld 61 to a point 64 on the under surface of the rail 60 beyond the thermit weld 61, an echo pulse rebounds from the point 64 and follows a signal path 65 avoiding the receiving transducer 66 in the probe 8. A display such as that shown in FIG. 7 appears on a cathode ray tube wherein a first blip 70 is produced by the pulse being transmitted from the transducer 62. In FIG. 8, the same testing device as shown in FIG. 6 is positioned above a rail 80 having a thermit weld 81 in the centre of the device. A pulse from the transmitting transducer 62 in probe 3 follows a signal path 82 which is interrupted by an area of porosity 83. Echo pulses from the area of porosity 83 are sent out in all directions, and one echo pulse follows signal path 84 which is received by the transducer 66 in probe 8. A display such as that shown in FIG. 9 appears on a cathode ray tube wherein a first blip 90 is produced by the pulse being transmitted from the transducer 62 and a second smaller blip 91 is produced by an echo pulse from the area of porosity 83 as received by the transducer 66.

Figure 10:
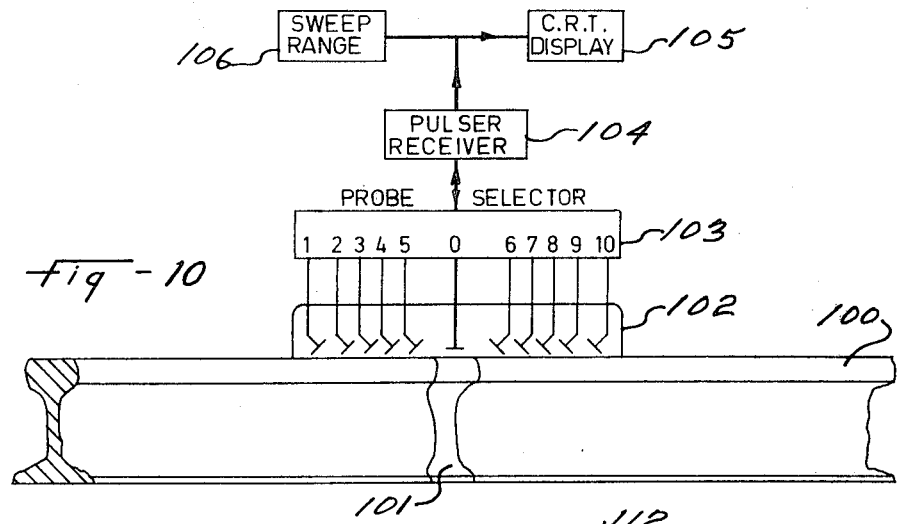
FIG. 10 is a block diagram of the circuit of an ultrasonic testing device of the type shown in FIG. 1, centred over a thermit rail weld.

The block diagram shown in FIG. 10 indicates a rail 100 having a thermit rail weld 101. A testing device 102 is shown centred over the weld 101 in the rail 100. The testing device 102 is similar to that shown in FIG. 1 and has probes 0 to 10. The leads from each of the transducers in the testing device 102 are fed to a probe selector 103 which is used for selecting which probe transmits and receives a pulse. For example, a pulse may be transmitted from outside probe 1 and received by outside probe 10. Thus, the probe selector would be set for transmit from 1, receive from 10, and a pulse transmitter and receiver 104 sends a pulse through to probe 1 and then receives it from probe 10. Similarly, the porosity seeking probes 2 to 9 may be selected. The signal from the pulse transmitter and receiver 104 is fed to a cathode ray tube display 105 which has a sweep range circuit 106 having a depth range control to govern the beam path distance displayed on the screen, a control to position the initial blip or zero shift on the screen, and a sensitivity level or gain control so the energy level is approximately the same for each weld inspected. For example, a pulse transmitted from outside probe 1 produces an initial blip on the display. There is then a time delay which is indicated by a gap on the display and then the echo pulse is received by outside probe 10, and is indicated on the display by a second blip spaced apart from the first blip. In some cases, particularly when using central probe 0, the probe acts as both the transmitter and receiver. It transmits a pulse and after the pulse rebounds off the under surface of the rail, it receives the echo pulse. Thus, the display indicates a transmittal blip and a receival blip, with the beam path distance in between representing the time it takes for the pulse to travel down through the rail, rebound off the under surface and the echo pulse to return to the transducer.

Figure 11:
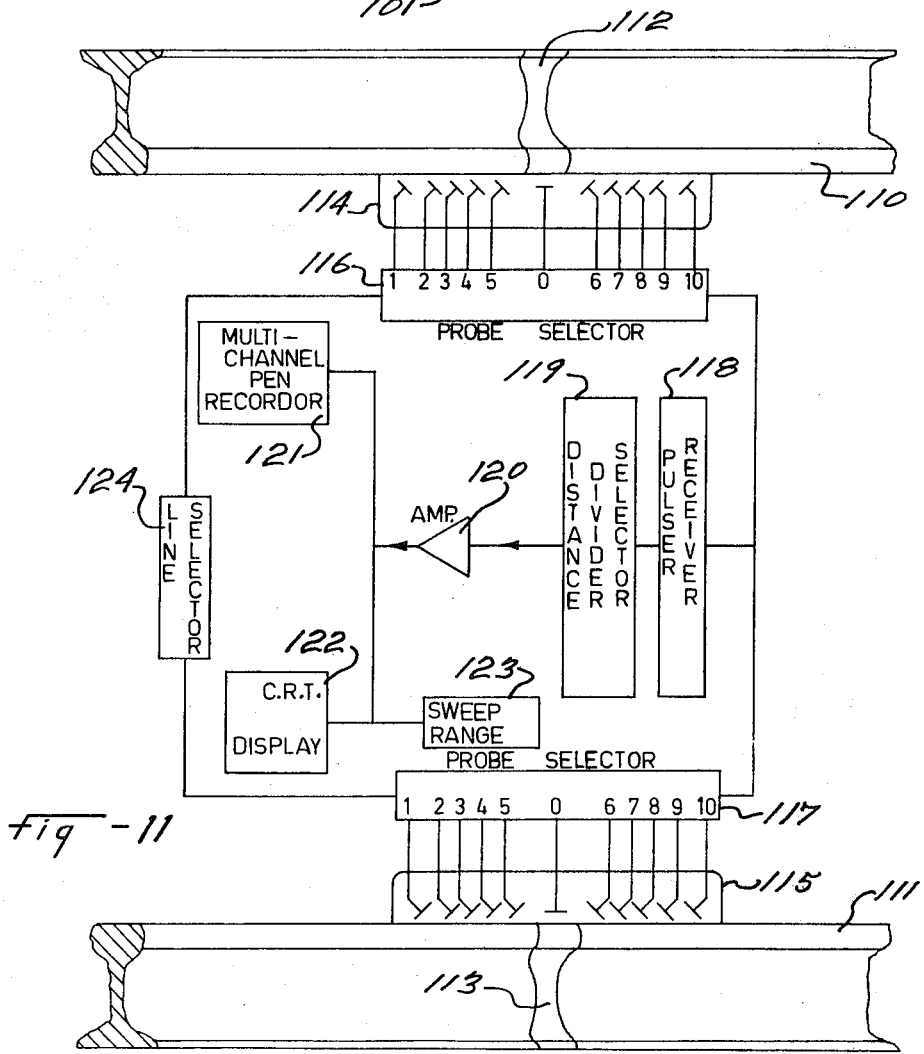
FIG. 11 is a block diagram of the circuit for two ultrasonic devices of the type shown in FIG. 1, centred above thermit rail welds in two rails, the devices being connected to an automatic monitoring system.

The block diagram shown in FIG. 11 indicates a pair of rails 110 and 111, each having thermit welds 112 and 113 therein. Testing devices 114 and 115, similar to that shown in FIG. 1, are positioned above the thermit welds 112 and 113 on the rails 110 and 111. Each transducer in the two testing devices 114 and 115 feed probe selectors 116 and 117 and each pair of matching probes in the testing devices requires a separate pulse which is transmitted and received by a pulser receiver module 118. Attached to this module 118 is a distance divider selector 119 to channel each pulse from each pair of probes through an amplifier 120 to a permanent record chart, namely a multi-channel pen recorder 121. The distance divider selector 119 includes a circuit to limit spurious signals passing to the multi-channel pen-recorder 121. Thus, the signals passed to the recorder 121 are either pulses or no-pulses which can be interpreted as a fault or no-fault in a rail weld. The signal from the distance divider selector 119 may also be passed to a cathode ray tube display 122 which is fitted with its own sweep range circuit 123 for controlling the blips on the display. A line selector 124 is fitted between the probe selectors 116 and 117 to insure the indication on the display and on the multi-channel pen-recorder 121 shows whether the pulse signal comes from rail 112 or rail 113.

A system such as that shown in FIG. 11 may be mounted on a rail test car and moved along a track at speeds of at least 5 miles an hour and in some cases higher. The cathode ray tube display 112 is used primarily for calibrating the testing devices. It would not be possible to see faults in a rail weld on the display when the devices were moving as the blips on the display would be constantly changing. The multi-channel pen-recorder 121 records the echo pulses on a chart; thus, the chart can be examined after the test run to determine which welds are defective, and the type of defect encountered. This is initially seen by a lack of echo pulse in one of the outside probes. To determine whether the faults were lack of fusion or porosity in the weld, an operator refers to the porosity seeking probe signals which are also recorded on the multiple pen-recorder chart. Central probe 0 indicates when the centre of each testing device is over a weld because at the time it passes over the weld it loses its bottom signal. This is indicated on the chart which also shows whether any echo pulses were received by probes 6, 7, 8 and 9. From this information an operator knows whether there is any porosity in a weld. After a rail test car has passed over a section of track, defective welds are noted, and a separate crew with a manual test device of the type shown in FIG. 6 may be sent out to double check the defective welds, and pinpoint the exact location and precise extent of the defects, since it may be prudent to leave a slightly defective weld and keep it under observation at regular intervals to ensure its condition is stable.

The testing device shown in FIG. 1 and incorporated in systems shown in FIGS. 10 and 11, is primarily suitable for the testing of thermit welds in rails; however, it may also be used for determining faults in rails, using the combination of a reflection and transparency method as described herein. In temperatures which are below freezing, the liquid used to provide a liquid film between the probe and the rail surface is preferably a light oil.

The embodiments of the invention in which an exclusive property or privilege is claimed are defined as follows:

1. Ultrasonic testing device for inspecting thermit rail welds in a track comprising
   a longitudinal shoe adapted to be placed lengthwise along the top surface of a rail;
   a first means for transmitting an ultrasonic energy pulse in a downwards path towards a location on the under surface of the rail;
   a first means for receiving an ultrasonic energy pulse and for receiving an echo of the transmitted pulse reflecting from the location on the under surface of the rail, said first transmitting means and said first receiving means being spaced a predetermined distance apart along said shoe and said location on the under surface of the rail being below the midpoint between said first transmitting means and said receiving means said first transmitting and receiving means for detecting porosity and a lack of fusion in the rail weld;
   a central transducer means positioned midway between said first transmitting means and said first receiving means for transmitting and receiving an ultrasonic energy pulse in and from a vertically downward direction, respectively for detecting the location of a rail weld;
   a plurality of second transmitting means located between said first transmitting means and said central transducer means for transmitting and directing an ultrasonic energy pulse at an acute angle to the top surface of the rail to cover the height of a rail directly under said central transducer means;
   a plurality of second receiving means for receiving ultrasonic energy pulses corresponding and equal in number to said second transmitting means and located between said central transducer means and said first receiving means, each second receiving means having a combination of spacing from the other said second receiving means, of spacing from said corresponding transmitting means, and of receiving an ultrasonic energy pulse at predetermined angles such that the pulses that are received are those pulses transmitted by said corresponding transmitting means which have been reflected by an area of porosity located substantially under said central transducer means, said corresponding pairs of second transmitting and receiving means for detecting porosity of the weld and the height in the rail of any determined areas of porosity;
   and means for indicating the transmission of each pulse, the receiving of the echos of the respective pulses, and the time interval for the pulses to pass downward through the rail and the echos of the respective pulses to pass upward through the rail.

2. The testing device according to claim 1 wherein the first means for transmitting the first means for receiving an ultrasonic energy pulse are outside transducers mounted on angular prisms for both transmitting the pulse at an angle of at least 45° through the weld and receiving a transmitted pulse and wherein the ultrasonic pulse may be transmitted from either outside transducer and the echo of the pulse received by the other outside transducer.

3. The testing device according to claim 2 and said central transducer means including a central transducer mounted on a flat prism positioned midway between the two outside transducers, the central transducer pointing vertically downwards and being adapted to both transmit and receive and ultrasonic energy pulse.

4. The testing device according to claim 3 including a plurality of porosity seeking transducers mounted on angular prisms positioned between one outside transducer and the central transducer and a similar number positioned between the other outside transducer and the central transducer, the porosity seeking transducers adapted to transmit and receive an ultrasonic energy pulse and to direct the pulse to cover the height of a rail directly under the central transducer, and selecting means to select the transducers to transmit and receive the electronic pulses.

5. The testing device according to claim 4 wherein the longitudinal shoe containing the transducers and prisms has a sheet metal housing having a spring means adapted to press the prisms against the top surface of a rail.

6. The testing device according to claim 4 wherein a liquid supply is provided together with a means to provide a thin liquid film between the prisms and the top surface of a rail.

7. The testing device according to claim 1 wherein the means for indicating the transmission of the pulse, the receiving of the echo of the pulse and the time interval for the pulse to pass downward through the rail and the echo of the pulse to pass upward through the rail is a cathode ray tube display fitted with a sweep range circuit.

8. The testing device according to claim 4 wherein four porosity seeking transducers mounted on angular prisms are positioned between one outside transducer and the central transducer and four further porosity seeking transducers are positioned at similar distances from the central transducer, between the other outside transducer and the central transducer.

9. The testing device according to claim 1 when incorporated with a second similar testing device mounted in a rail test car, one device positioned over each rail and including a line selector adapted to select transducers in either device for transmitting and receiving an electronic pulse and including a multi-channel pen-recorder adapted to produce a permanent record chart representing test results graphically.

10. The testing device according to claim 9 including a distance divider selector adapted to limit spurious signals passing to the multi-channel pen-recorder and pass only signals or non-signals indicating a defect in a rail weld.

11. A method of inspecting a thermit rail weld in a track comprising
    transmitting a first ultrasonic energy pulse from the top of the track at one side of the thermit rail weld at an angle of at least 45° through the weld,
    transmitting a second ultrasonic energy pulse from the top of the track above the thermit rail weld vertically downward through the weld,
    transmitting a plurality of third ultrasonic energy pulses from different locations along the top of the track between the transmitting locations of said first pulse and said second pulse, said third pulses being transmitted at an angle of at least 45° through the weld and each third pulse being transmitted in a path which passes through a different height position of the weld,
    detecting at locations on the top of the track on the other side of the weld any echo pulses from said transmitted first pulse, second pulse and third pulses,
    determining on the basis of said detected pulses whether said weld has a lack of fusion and whether said weld has porosity.

12. A method as claimed in claim 11 and further including jointly moving the locations along the rail where said first pulse, second pulse and third pulses are transmitted while maintaining the relative distances between said locations constant and repeating the transmitting and detecting steps during said movement; and
    recording the detected echo pulses and the fact that echo pulses were not detected on a multi-channel chart, one channel being used for each of the first and second transmitted pulses and for each of the plurality of third transmitted pulses.

* * * * *